US00PP34071P2

(12) United States Plant Patent
Karniel

(10) Patent No.: US PP34,071 P2
(45) Date of Patent: Mar. 29, 2022

(54) SEEDLESS GRAPEVINE NAMED 'ARDTHIRTYFIVE'

(50) Latin Name: *Vitis vinifera*
Varietal Denomination: ARDTHIRTYFIVE

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: AGRICULTURAL RESEARCH AND DEVELOPMENT LIMITED LIABILITY COMPANY, Bakersfield, CA (US)

( * ) Notice: Subject to any disclaimer, the term of this patent is extended or adjusted under 35 U.S.C. 154(b) by 0 days.

(21) Appl. No.: 17/300,598

(22) Filed: Aug. 30, 2021

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88
See application file for complete search history.

*Primary Examiner* — Anne Marie Grunberg
(74) *Attorney, Agent, or Firm* — Lewis Roca Rothgerber Christie LLP

(57) ABSTRACT

A new distinct variety of grapevine named 'ARDTHIRTY-FIVE' abundantly forms attractive crunchy seedless berries with a red skin coloration; medium density in large clusters which display a naturally sweet flavor, commonly ready for harvesting during July in San Joaquin Valley of Central Calif., U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has a varietal denomination 'ARDTHIRTYFIVE'.

BACKGROUND OF THE INVENTION

A breeding program was initiated during the late 1990's near Bakersfield in San Joaquin Valley of Central Calif. In 2013, during this breeding program, a new variety of *Vitis vinifera* was created by deliberate cross breeding of two parent plants by emasculation of the pollen bearing organ of the female and introducing pollen from another male origin. The female parent of the new variety was 10-10+2, which is a very fertile and crispy seedless white table grape variety (non-patented in the United States). The male parent (i.e. the pollen parent) of the new variety was 25-51+2, a naturally sweet and crisp seedless red variety (non-patented in the United States).

TABLE 1

ARDTHIRTYFIVE compared with parents & closely related variety:

| | ARDTHIRTY-FIVE | 10-10+2 (Maternal) | 25-51+2 (Paternal) | Flame (unpatented in the United States) |
|---|---|---|---|---|
| Berry shape | Broad ellipsoid | Cylindrical | Broad ellipsoid | Globose |
| Berry color | Red | White | Red | Greyish red |
| Bunch density | Lax | Medium | Medium | Tight |

The parentage of the new variety can be summarized as follows:

10-10+2 X 25-51+2

An artificial pollination was created, and the result was an embryo which possessed unique genetic qualities. The rudiments resulting from the above pollination were embryo rescued. In 2014 the plant was transplanted to Bakersfield in San Joaquin Valley of Central Calif.

It was found that the new grapevine of the present invention possesses the following combination of characteristics:

(a) Forms attractive crunchy seedless berries with a red skin coloration; in medium density, large clusters which display a naturally sweet flavor,
(b) Commonly bears fruit during the month of July in the San Joaquin Valley of Central California, U.S.A., and
(c) Bears fruit that is firm and is well amenable for storage, handling, and shipping.
(d) Produces 40 bunches per vine, and an average of about 1-2 bunches per shoot, at a total of 48 lbs fruit per vine.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2015 near Bakersfield in the San Joaquin Valley of Central Calif., U.S.A. by bud grafting on mature Thompson rootstock (non-patented in the United States). Such asexual propagation has been conducted thereafter in successive years to date and has shown that the characteristics of the new variety are strictly transmissible from one generation to another. Accordingly, the new variety undergoes asexual propagation in a true to type manner.

SUMMARY OF THE INVENTION

The new variety ARDTHIRTYFIVE is a red seedless table grape with a high production, e.g., about 40 bunches per vine, and an average of about 1-2 bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical six-year-old specimens of the new variety, vegetatively propagated, in color as nearly true as it is reasonably possible to make in a color illustration of this character. Colors in the photograph may differ from the color values cited in the detailed botanical description below, which accurately describes the colors of the new Grapevine.

The drawing shows leaves, stems and grapes of ARDTHIRTYFIVE.

DETAILED BOTANICAL DESCRIPTION

The chart used in the identification of colors is The R.H.S. Colour Chart of The ROYAL HORTICULTURAL SOCIETY (3rd Edition). The description is based on the observation of plants growing on 'Thompson Seedless' rootstock outdoors near San Joaquin Valley of Central California, U.S.A.

| VINE CHARACTERISTICS: | |
|---|---|
| vigor | Vigorous upright shoots |
| productive capacity | Bearing at a natural, average capacity. Spur pruning. |
| trunk | Strong and developed. Diameter is 3.3 inches, measured at 5.2 inches above ground. Rough with a fibrous, shaggy exterior. Light maple brown coloring (greyed orange 177C) |

Date of bud burst in Bakersfield Calif.: February 24th.

| YOUNG SHOOT CHARACTERISTICS: | |
|---|---|
| Openness of tip | wide open |
| Density of prostrate hairs on tip | absent or very sparse |
| Anthocyanin coloration of prostrate hairs on tip | none (yellow green 144A) |
| Density of erect hairs on tip | medium |

| YOUNG LEAF CHARACTERISTICS: | |
|---|---|
| Color of upper side of blade | yellow green 144A |
| Color of lower side of blade | yellow green 144B |
| Density of erect hairs between main veins on upper side of blade | sparse |

-continued

| YOUNG LEAF CHARACTERISTICS: | |
|---|---|
| Density of erect hairs between main veins on lower side of blade | sparse |
| Density of prostrate hairs on main veins on upper side of blade | sparse |
| Density of prostrate hairs on main veins on lower side of blade | sparse |

| SHOOT CHARACTERISTICS: | |
|---|---|
| Attitude (before tying) | semi-erect |
| Color of dorsal side of internodes | yellow green 144B |
| Color of ventral side of internodes | yellow green 152B |
| Color of dorsal side of nodes | yellow green 145A |
| Color of ventral side of nodes | yellow green 151A |
| Density of erect hairs on internodes | absent or very sparse |
| Density of prostrate hairs on internodes | sparse |
| Length of tendrils | 3.5 inches |
| Diameter of tendrils | 0.04 inches |
| Color of tendrils | yellow green 153A |
| Number of tendrils at bloom | 3 |
| Positioning of first flowering and fruiting node | the first bunch is in the 3rd node |
| Inflorescence number per flowering shoot | 1-2 |

| FLOWER CHARACTERISTICS: | |
|---|---|
| Reproductive organs | fully developed stamens and fully developed gynoecium |
| Flower length | 0.3 inches |
| Flower diameter | 0.15 inches |
| Pistil length | 0.1 inches |
| Pistil color | green 143B |
| Pollen Amount | poor |
| Pollen color | yellow 6A |
| Stamen color | yellow green 144A |
| Stamen length | 0.1 inches |
| Number of stamen | 5 |

First bloom in Bakersfield, Calif.: May 1st.

Date of full bloom in Bakersfield, Calif.: May 9th.

| MATURE LEAF CHARACTERISTICS: | |
|---|---|
| Size of blade | 5.5 × 5.5 inches |
| Shape of blade | pentagonal |
| Base descriptors | pentagonal |
| Leaf margin | doubly serrate |
| Leaf apex | acute |
| Blistering of upper side of blade | absent or very sparse |
| Depth of upper lateral sinuses | shallow |
| Number of lobes | three |
| (Only varieties with lobed leaves) | |
| Arrangement of lobes of upper lateral sinuses | closed |
| Arrangement of lobes of petiole sinus | wide open |
| Length of teeth | 0.6 inches |
| Ratio length/width of teeth | large |
| Shape of teeth | both sides convex |
| Density of prostrate hairs between main veins on lower side of blade | absent or very sparse |
| Density of erect hairs on main veins on lower side of blade | absent or very sparse |

-continued

| MATURE LEAF CHARACTERISTICS: | |
|---|---|
| Density of erect hairs between the main veins on upper side of blade | absent or very sparse |
| Density of prostrate hairs on main veins on upper side of blade | absent or very sparse |
| Length of petiole compared to length of middle vein | equal |
| Top side color | green 137B |
| Bottom side color | yellow green 147B |
| Texture of upper side of blade | rough |
| Texture of lower side of blade | rough |
| Vein color on upper blade | yellow green 145A |
| Vein color on lower blade | yellow green 145C |
| Venation pattern for upper blade | netlike venation |
| Venation patten for lower blade | netlike venation |
| Petiole length | 5 inches |
| Petiole diameter | 0.1 inches |
| Petiole color | yellow green 144B |
| Petiole texture | rough |

Date of beginning of berry ripening in Bakersfield Calif.: July 4$^{th}$.

| BUNCH CHARACTERISTICS: | |
|---|---|
| Size (peduncle excluded) | large |
| Density of berries on bunch | lax |
| Bunch length | 8 inches |
| Bunch diameter | 6 inches |
| Length of peduncle of primary bunch | 2.4 inches |
| Diameter of peduncle of primary bunch | 0.15 inches |
| Peduncle of primary bunch color | yellow green 145B |
| Peduncle texture | smooth |
| Bunches per vine | 40 |
| Average bunch weight | 1.2 lbs |

| BERRY CHARACTERISTICS: | |
|---|---|
| Size | medium |
| Length | 1 inch |
| Weight | 0.3 oz |
| Diameter | 0.8 inches |
| Shape | broad ellipsoid |
| Color of skin (without bloom) | greyed red 180A |
| Flesh color | greyed green 193D |
| Brix | 19 |
| Titrabable acidity percentage | 3.9% |
| Juice | 3.6 ph |
| Ease of detachment from pedicel | moderately easy |
| Thickness of skin | medium |
| Anthocyanin coloration of flesh | none |
| Firmness of flesh | very firm |
| Particular flavor | natural, sweet |
| Formation of seeds | rudimentary |
| Berries per bunch | 106 |

| PEDICEL CHARACTERISTICS: | |
|---|---|
| Length | 0.6 inches |
| Diameter | 0.1 inches |
| Color | yellow green 145A |
| Pedicel texture | rough |

| WOODY SHOOT CHARACTERISTICS: | |
|---|---|
| Woody shoot texture | smooth |
| Woody shoot color | greyed orange 165B |
| Woody shoot length | 72 inches |
| Diameter | 0.4 inches |
| Internode length | 3.5 inches |

Market use of observed plants: Fresh market.

Age and growing conditions: Six years growing under Y system in South Joaquin Valley (hot, dry summers).

Shipping characteristics: Fruit was in cold storage. Stored in poly bags inside Styrofoam boxes with sulfur pads. After 30 Days: rachises were 10% green; 2% berry shattering; no berry wrinkling or cracks were apparent.

DNA profile: To further the characterize the new variety DNA was extracted from plant samples and a DNA profile was obtained at California Seed & Plant Lab, California USA using base pairs for 10 standard microsatellite DNA markers. The data is presented hereafter.

TABLE 2

DNA profile for ARDTHIRTYFIVE

| Microsatellite DNA Marker | Allele Sizes in Base Pairs | |
|---|---|---|
| M1 | 228 | 234 |
| M2 | 249 | 249 |
| M3 | 179 | 194 |
| M4 | 212 | 216 |
| M5 | 273 | 273 |
| M6 | 145 | 151 |
| M7 | 187 | 205 |
| M8 | 247 | 255 |
| M9 | 214 | 214 |
| M10 | 247 | 247 |

The ARDTHIRTYFIVE variety has not been observed under all possible environmental conditions to date. Accordingly, it is possible that the phenotypic expression may vary somewhat with changes in light intensity and duration, cultural practices, and other environmental conditions.

Additional information relating to plant and fruit disease and pest resistance or susceptibility has not been observed to date. Specification of the plant hardiness zone and the heat/cold resistance has not been observed to date.

What is claimed is:

1. A new and distinct grapevine, botanically known as *Vitis vinifera*, identified as 'ARDTHIRTYFIVE', substantially as shown and described herein.

* * * * *

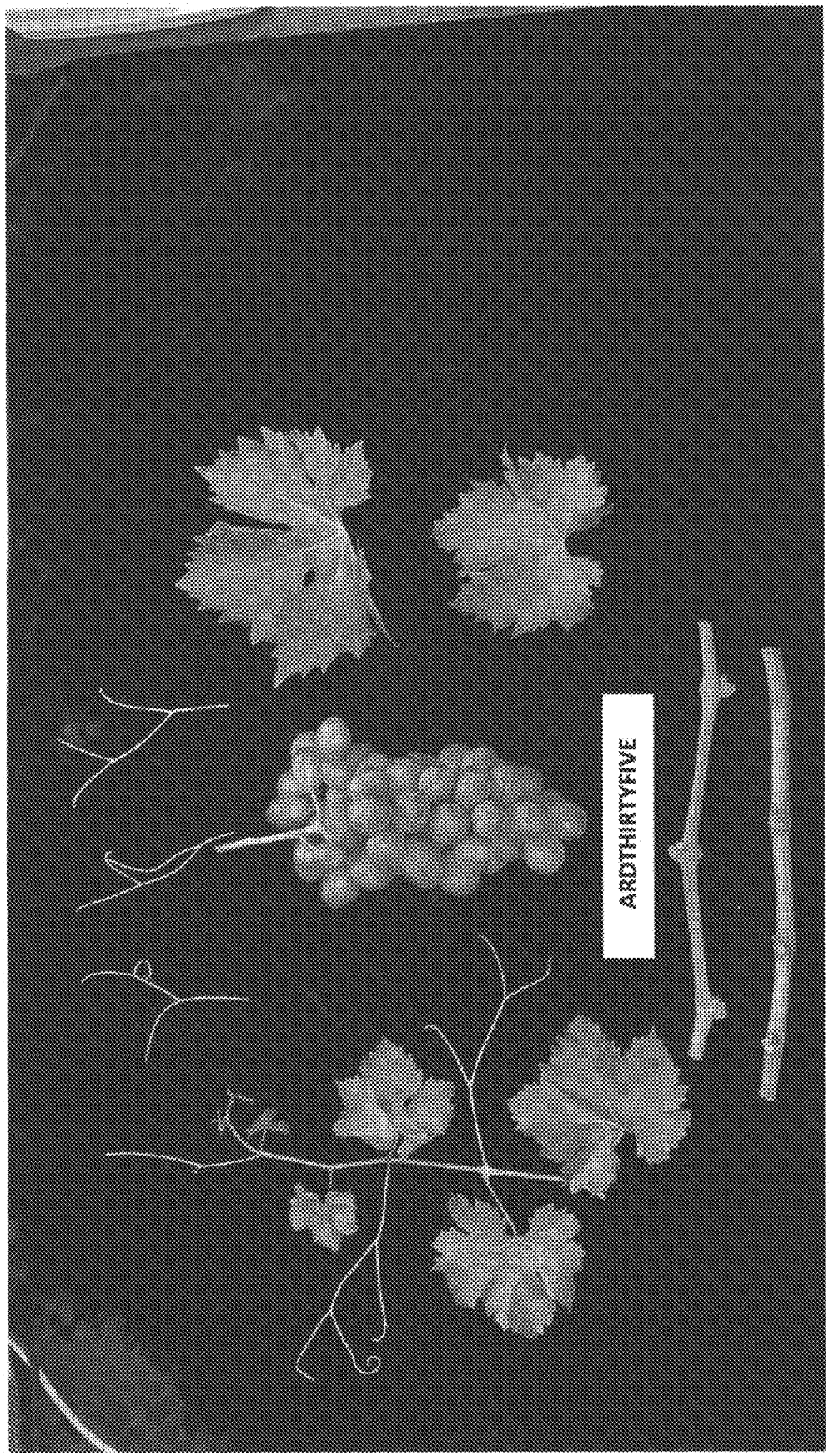
ARDTHIRTYFIVE